United States Patent [19]

Paglione

[11] Patent Number: 5,585,733
[45] Date of Patent: Dec. 17, 1996

[54] CAPACITIVE SENSOR AND METHOD OF MEASURING CHANGES IN CAPACITANCE

[75] Inventor: Robert W. Paglione, Mercer, N.J.

[73] Assignee: David Sarnoff Research Center, Princeton, N.J.

[21] Appl. No.: 480,362

[22] Filed: Jun. 7, 1995

Related U.S. Application Data

[63] Continuation of Ser. No. 218,285, Mar. 25, 1994, abandoned, which is a continuation-in-part of Ser. No. 943,080, Sep. 10, 1992, abandoned.

[51] Int. Cl.$^6$ ................................. G01R 27/26
[52] U.S. Cl. .................... 324/678; 324/676; 324/679
[58] Field of Search .................... 324/658, 676, 324/678, 679, 690; 340/870.37

[56] References Cited

U.S. PATENT DOCUMENTS

| | | | |
|---|---|---|---|
| 3,581,196 | 5/1971 | Spaid | 324/678 |
| 3,761,805 | 9/1973 | Dornberger | 324/677 |
| 3,824,459 | 7/1974 | Uchida | 324/678 |
| 4,103,225 | 7/1978 | Stephens | 324/678 |
| 4,149,231 | 4/1979 | Bukosky | 324/678 |
| 4,404,481 | 9/1983 | Ide | 324/678 |
| 4,558,274 | 12/1985 | Carusillo | 324/678 |
| 4,587,850 | of/1986 | Moser | 73/658 |
| 4,788,489 | 11/1988 | Kobayashi | 324/61 P |
| 4,825,147 | 4/1989 | Cook | 324/678 |
| 4,961,055 | 10/1990 | Habib | 324/662 |
| 5,051,921 | 9/1991 | Paglione | 364/509 |
| 5,294,889 | 3/1994 | Heep et al. | 324/678 |
| 5,446,444 | 8/1995 | Lease | 324/658 X |
| 5,461,321 | 10/1995 | Sanders et al. | 324/678 |

FOREIGN PATENT DOCUMENTS 1049827  7/1982  U.S.S.R. ................. 324/678

OTHER PUBLICATIONS

F. Guthen Elektor vol. 5, No. 10 Oct. 1979 pp. 10/16–10/19, "DIGIFARAD".
Mahmud et al. IEEE Trans. on Inst and Meas. vol. 37, No. 2, Jun. 1988, pp. 191–194, "A Microprocessor Based Switched Battery Capacitance Meter".

*Primary Examiner*—Maura K. Regan
*Assistant Examiner*—Glenn W. Brown
*Attorney, Agent, or Firm*—William J. Burke

[57] ABSTRACT

An apparatus and method for measuring the variation in the capacitance of a capacitive sensor. The apparatus and method include means for constantly applying a constant electrically current to an electrode of the capacitor and means for generating a first series of timing pulses. The voltage on the capacitor is compared to a reference voltage and an electrical signal is generated when the voltage on the capacitor reaches a first voltage which exceeds the reference voltage. The first series of timing pulses emitted by the generating means from the time that the charging of the capacitor beings until the electrical signal is generated is counted and an output signal is generated corresponding to the number of timing pulses counted. An application of the sensor to the measurement of the change in length of a telescoping device such as a shock absorber is also disclosed.

4 Claims, 5 Drawing Sheets

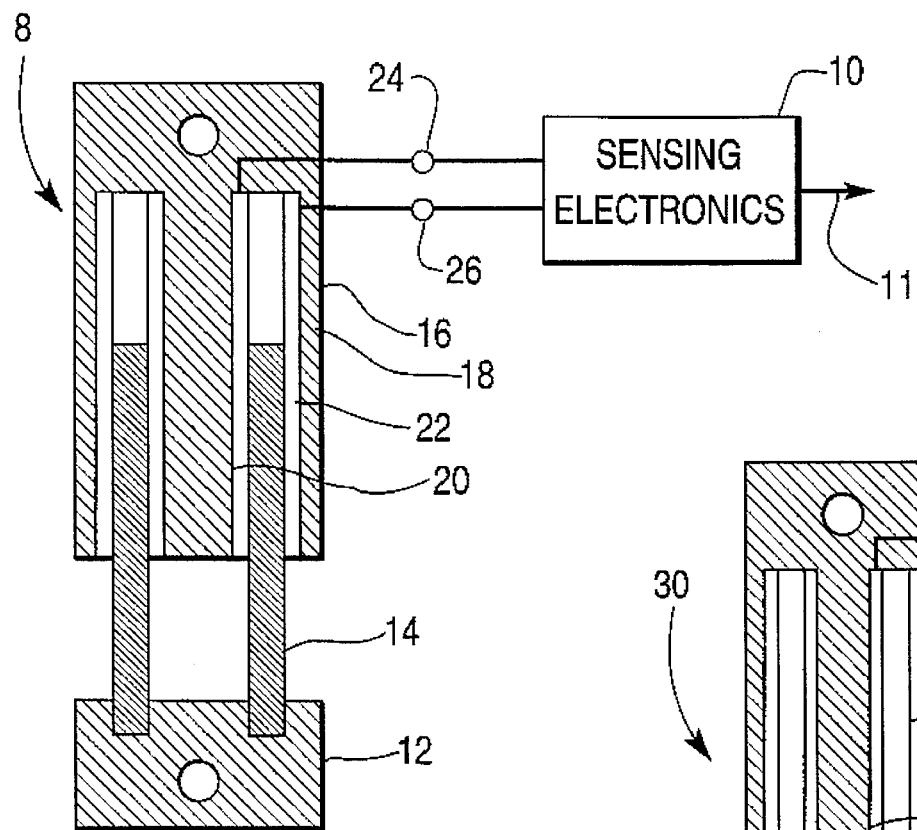
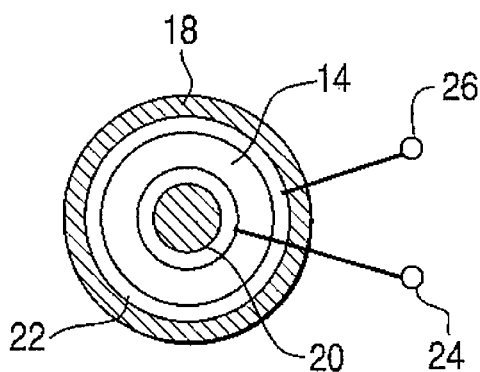
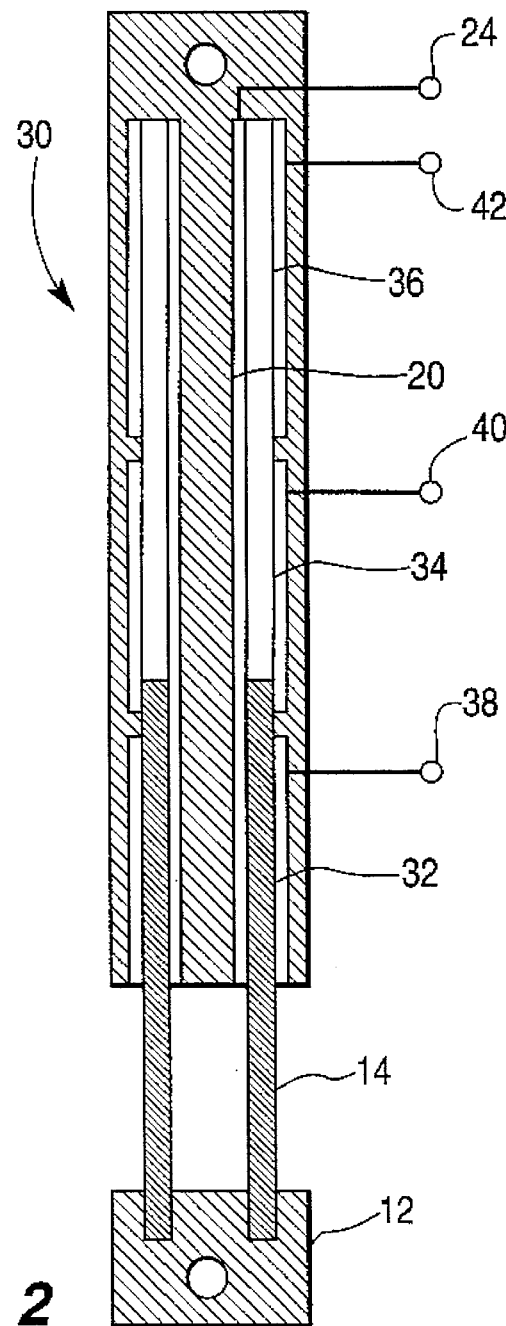
FIG. 1a
FIG. 1b
FIG. 2

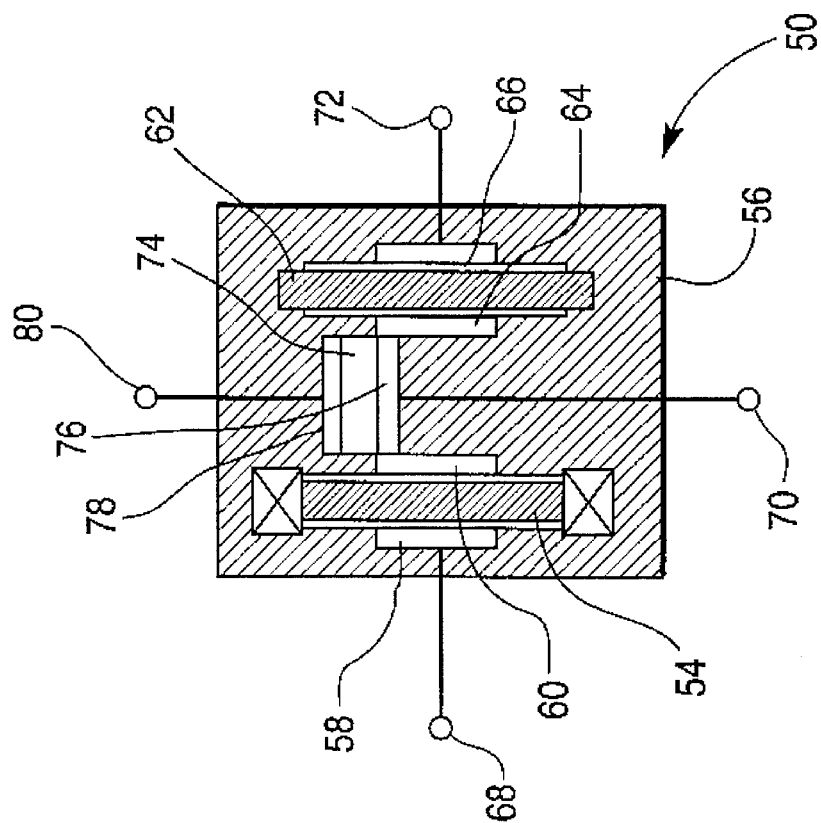
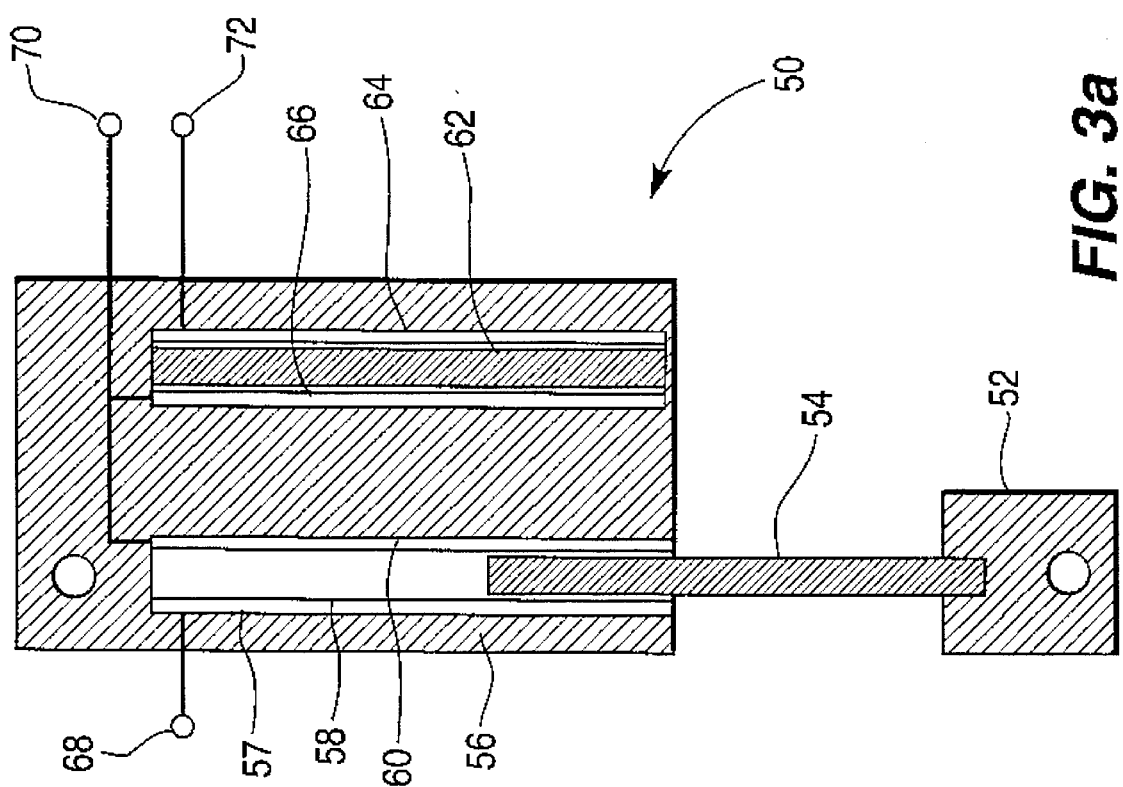
FIG. 3b
FIG. 3a

CAPACITIVE SENSOR AND METHOD OF MEASURING CHANGES IN CAPACITANCE

This is a continuation of application Ser. No. 08/218,285, filed Mar. 25,1994, now abandoned, which is a continuation-in-part of application Ser. No. 07/943,080, filed Sep. 10, 1992, now abandoned.

The invention relates to an apparatus and method for measuring the capacitance of a capacitive sensor and, more particularly, to the measurement of variations in the capacitance of the sensor.

BACKGROUND OF THE INVENTION

The use of capacitive sensors to measure a change in dimension of an object such as a telescoping device having a variable dimension are known. Moser in U.S. Pat. No. 4587850 discloses apparatus for detecting and measuring the motion of a piston in a cylinder, including a variable impedance comprising a dielectric moving between the fixed electrodes. The extent of the motion of the dielectric into the space between the electrodes provides a measure of the motion of the piston. The change in the magnitude of the capacitor is determined using a capacitance bridge, such as a Wheatstone bridge. A reference capacitor is also provided to compensate for changes in the variable capacitor arising from changes in temperature and other ambient conditions. Measuring circuitry such as that disclosed by Moser can be realized using a microprocessor to switch in various combinations of capacitors for the variable capacitor while balancing the bridge. A look-up table in the microprocessor then provides an output code for the voltage corresponding to the value of the measured capacitance. This type of circuit is difficult to reduce to a single monolithic integrated circuit due to the large values and number of capacitors used and requires extra components to produce a linear electrical output with change in dimension or distance traveled.

It would be desirable to have an electronic system to measure the variation in capacitance having an electrical output which is linear with the change in capacitance and which can be implemented in an integrated circuit.

SUMMARY OF THE INVENTION

The invention is an apparatus for measuring the capacitance of a capacitive sensor comprising means for charging the capacitor; means for generating an electrical signal when the capacitor is charged to a certain voltage; and means for generating an output sisal corresponding to the time required to charge the capacitor to the certain voltage.

The invention is also a method of measuring the capacitance of a capacitor comprising the steps of charging the capacitor; measuring the time required to charge the capacitor to a first voltage; and generating an output signal linearly proportional to the time required to charge the capacitor to the first voltage.

BRIEF DESCRIPTION OF THE DRAWING

FIGS. 1(a) and 1(b) are cross-sectional views of a capacitive sensor including a sensor body and electronics.

FIGS. 2 is a cross-sectional view of another sensor body.

FIGS. 3(a) and 3(b) are cross-sectional views of another sensor body.

DETAILED DESCRIPTION

Figure 4:
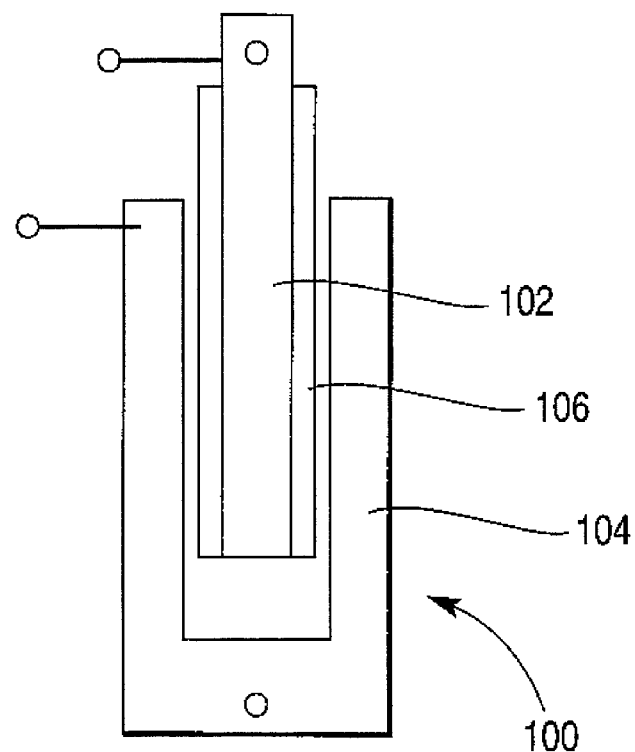
FIGS. 4 is a cross-sectional view of another sensor body.

Elements common to different Figures have the same numerical designation in each Figure.

In FIG. 1 a capacitive sensor of the invention comprises a sensor body 8 containing a variable capacitor and electronics 10 to provide an electronic output signal 11 proportional to, and preferably linear with, a change in the value of the capacitor. The sensor body 10 comprises a piston 12 with a dielectric sleeve 14 mounted thereon, a body 16, and a cylindrical opening 18 extending a distance into the body 16 from an end thereof. The inner and outer walls of the cylindrical opening 18 are covered with electrically conductive layers 20 and 22, respectively, which form the electrodes of a capacitor. The electrically conductive layers 20 and 22 are connected to the external electrodes 24 and 26 respectively. The electrodes 24 and 26 are connected to the input terminals of the electronics 10. As the piston moves along the cylindrical axis of the sensor body, the dielectric 14 moves in and out of the opening 18 thereby changing the value of the capacitor. The electronics 10 measure the capacitance and produce an output voltage or pulse-width-modulated signal which is preferably linearly proportional to the value of capacitance. The measurement of the change in the capacitance provides a direct measure of the distance moved by the piston 12.

The body 16 is typically a cylinder preferably formed of a material such as Kapton or Mylar with screened-on conductors as the layers 20 and 22. Plated plastic parts of any suitable shape could be used. In a preferred embodiment the electrodes of the sensor capacitor are fixed and an insulating dielectric attached to the moving member moves in and out of the fixed capacitor to effect the capacitance change. An advantage of this arrangement is that the external electrical connections to the sensor body do not flex as the motion occurs, thereby simplifying the structure of these connections and greatly increasing their reliability and that of the system as a whole.

In FIG. 2 a sensor body 30 includes an electrically conductive layer, corresponding to the layer 22 of FIG. 1, which is divided into three separate, unconnected conductive layers 32, 34 and 36. The conductive layers 32, 34 and 36 together with the electrically conductive layer 20 form the capacitor electrodes of three separate capacitors. The electrically conductive layers 32, 34 and 36 are connected to the external electrodes 38, 40 and 42 respectively.

The first capacitor, formed by layers 20 and 32, is always filled with the dielectric body 14 regardless of the position of the piston 12, thus providing a reference capacitor which can be used to measure, and correct for, wear, temperature variations and other effects which might change the characteristics of the dielectric and, thus, the magnitude of the capacitor.

The second capacitor, formed by layers 20 and 34, corresponds to the capacitor of FIG. 1. As the piston moves along the cylindrical axis of the sensor body, the extent to which the body 14 fills the space between the layers 20 and 34 varies, thereby changing the value of the capacitor. The measurement of the change in the capacitance of this capacitor provides a direct measure of the distance moved by the piston 12.

The third capacitor, formed by layers 20 and 36, has any other material present in the sensor, for example an oil such as is used in a shock absorber, between the electrodes. The third capacitor, since it is always filled with the other material regardless of the position of the piston 12, provides a reference capacitor which can be used to measure, and correct for the change in the characteristics of such material and, thus, the magnitude of the capacitor.

In FIG. 3, a sensor body 50 containing a variable capacitor comprises a piston 52 with a dielectric slab 54 mounted thereon, a body 56, and a rectangular opening 57 extending a distance into the body 56 from an end thereof. Two opposed walls of the opening 57 are covered with electrically conductive layers 58 and 60, respectively, which form the electrodes of a capacitor. The electrically conductive layers 58 and 60 are connected to the first external electrode 68 and common electrode 70 respectively. As the piston moves along the axis of the opening 57, the dielectric body 54 moves in and out of the opening 57 thereby changing the value of the capacitor. The measurement of the change in the capacitance of this capacitor provides a direct measure of the distance moved by the piston 52.

The sensor body 50 also includes second and third reference capacitors to provide calibration of the sensor body due to changes in the characteristics of the variable capacitor due to wear, temperature variations and other effects which might change the characteristics of the dielectric and, thus, the magnitude of the capacitor or the characteristics of other materials such as an oil present in the sensor between the electrodes. The second capacitor comprises a dielectric body 62 of the same material as the body 54 between electrically conducting layers 64 and 66 which are connected to the common electrode 70 and the second external electrode 72, respectively. The third capacitor comprises a material 74, such as an oil, between electrically conducting layers 76 and 78 which are connected to the common electrode 70 and the third external electrode 80, respectively.

In FIG. 4 an alternative sensor body 100 comprises a piston 102, an outer metal cylinder 104 with a dielectric sleeve 106 therebetween. The magnitude C of the capacitor is:

$$C = \{2\pi\epsilon_k \epsilon_0 L\}/\ln(r_1/r_2)$$

where $r_1$ and $r_2$ are the outer and inner conductor radii, $\epsilon_k$ is the dielectric constant of the insulator, $\epsilon_0$ is the dielectric constant of free space equal to $8.85 \times 10^{-12}$ farads/meter, and L is the length of the capacitor. The sensor body was made using telescoping brass tubing as the electrodes and heat shrink fluorinated ethylene propylene (FEP) as the insulator. The dimensions of the sensor 10 were typically about $r_1 = 0.32$ cm, $r_2 = 0.109$ cm, $\epsilon_k = 2.1$, and L=15.25 cm. The maximum capacitance C is then equal to about 130 picofarads.

The invention comprises charging a capacitor from a constant current source. The capacitor charges at a uniform, linear rate and thus the voltage across the capacitor increases linearly during charging.

Alternatively the capacitor can be charged from a current or voltage source in a substantially linear way. In this case, the voltage V developed across the capacitor C as a function of time T is $$V = V_0(1 - e^{-(T/RC)}).$$

where $V_0$ is the asymptotic value of the voltage across the capacitor and R is the resistance across the capacitor. For T<<RC, the voltage is $$V \approx V_0(1-(1-T/RC)) = V_0 T/RC$$

$$C \approx (V_0 R/V)T = \text{constant } T$$

The capacitance is thus linearly proportional to the length of time required to charge the capacitor to a voltage V provided that T<<RC. The invention further comprises comparing the voltage developed across the capacitor to a reference voltage and generating a signal pulse once the voltage across the capacitor has reached a certain level. The invention further comprises measuring the time required to charge the capacitor, using for example counting means, and generating an output signal linearly proportional to the charging time T. The signal pulse resets the counter and latches the latch. The output of the latch in digital form can be used in apparatus (not shown) which accepts a digital signal. Alternatively the output of the latch can be converted to an analog signal.

Figure 5:
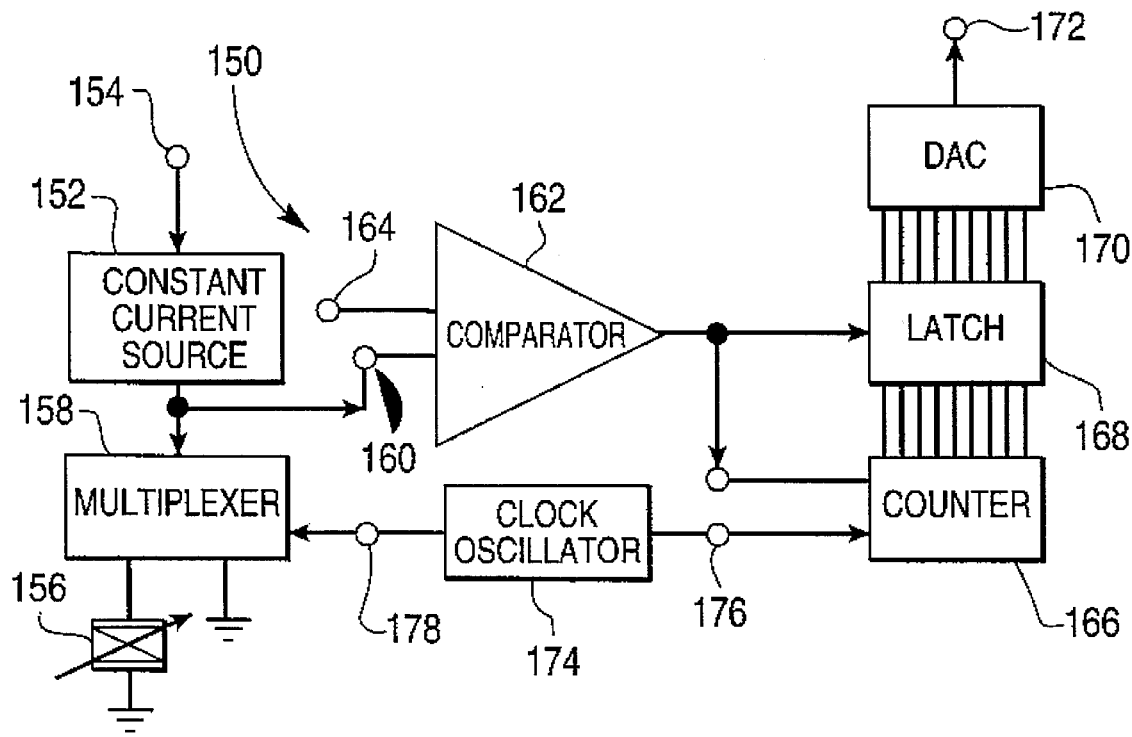
FIG. 5 is a block diagram of an electrical circuit for measuring capacitance.

A circuit 150 for measuring the change in capacitance is shown in FIG. 5 in block diagram form. A constant-current source 152 having an input electrode 154 connected to a power source such as a battery charges a variable capacitor 156 through a multiplexer 158. The multiplexer alternately connects the current source 152 to the electrode of the capacitor 156 and to a source of reference potential such as ground potential. The voltage V developed across the capacitor 156 is a linear ramp from 0 V with the slope of the ramp being proportional to the value of the sensor capacitance. The voltage V is also applied to a first input electrode 160 of a comparator 162. The comparator 162 changes output state when the voltage $V_c$ becomes greater than a reference voltage $V_{ref}$ applied to a second comparator input electrode 164. At this point the reading of counter 166 held in latch 168 is converted by digital to analog converter (DAC) 170 into a voltage and the counter 166 is reset. The clock oscillator 174 provides two synchronous outputs, a first series of high frequency pulses 176 and a second series of low frequency pulses 178. The first series 176 is counted by the counter 166 to provide the measure of time; the second series 178 switches the multiplexer 158, alternately connecting the input electrode of the variable capacitor 156 to the current source or to ground. The period of the second series must be long compared to the time T required to charge the capacitor 154. A DAC 170 converts the digital representation of the counts into a voltage at electrode 172. DAC 170 is not required if the device connected to electrode 172 accepts a signal in digital format.

Figure 6:
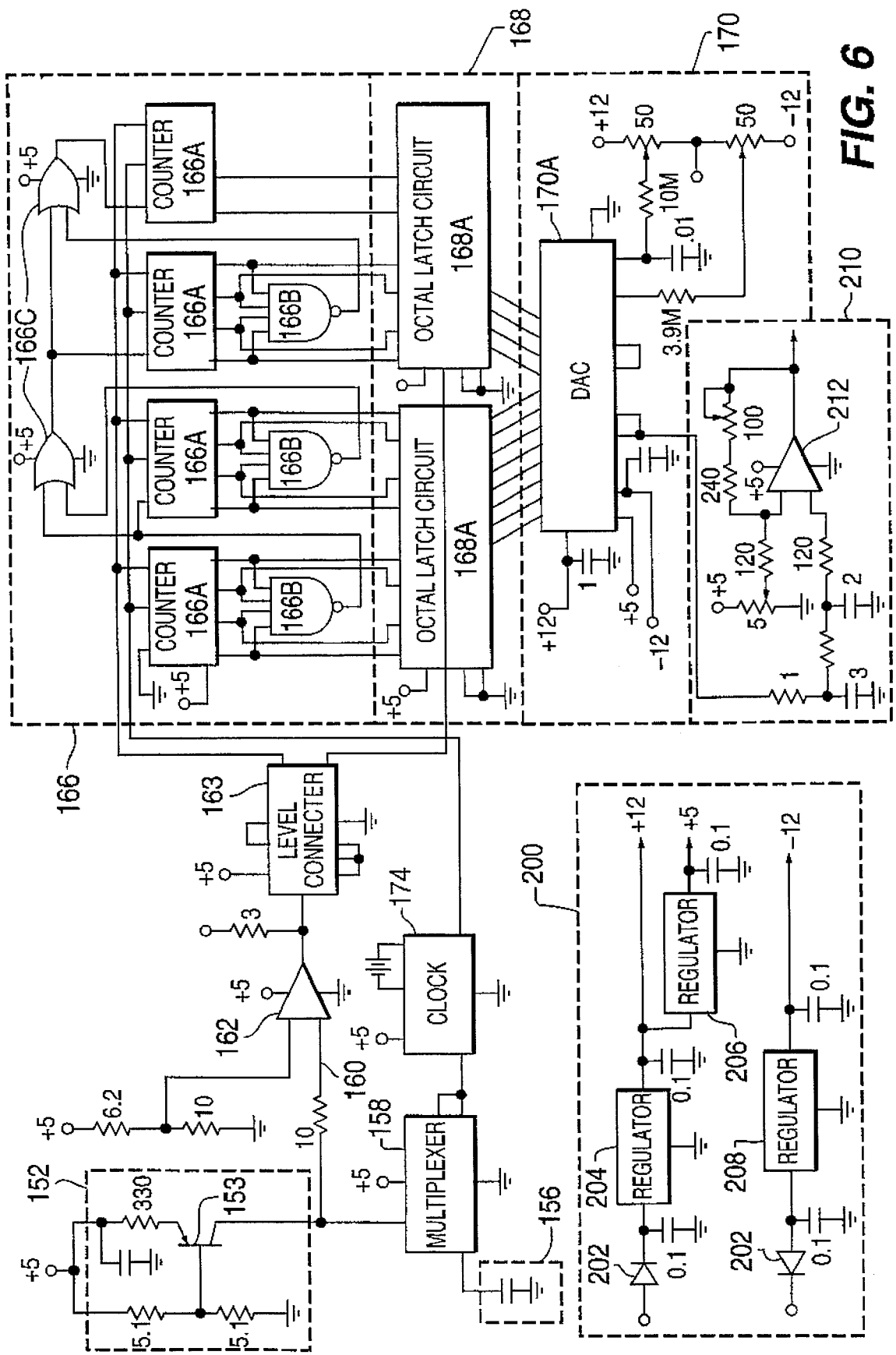
FIGS. 6 is a detailed circuit diagrams of an embodiment of the electrical circuit of FIG. 5.

In FIG. 6 a detailed implementation of the circuit of FIG. 5 is shown. In the Figure all resistors are in kilohms and all capacitors are in microfarads (μf) unless otherwise indicated. The circuit includes a constant-current source 152 including transistor 153, a variable capacitor 156, multiplexer 158, comparator 162, level converter 163, counter 166, latch 168, DAC 170, output section 210 and power supply 200. The clock 174 provides two synchronous outputs. The high-frequency output is counted by the counter; the low-frequency output switches the multiplexer 158. The multiplexer 158 alternately connects the capacitor 156 to the current source or to ground.

Transistor 153 is preferably a type 2N4250. Multiplexer 158 is preferably a type 74HC4053. Comparator 162 is preferably a type CA339. Level converter 163 is a Schmidt trigger used to sharpen the pulse output generated by the comparator 162. Converter 163 is preferably a type CD4093.

The output pulse from converter 163 resets counters 166 and latches the data of latches 168. Output section 210, including an operational amplifier 212, provides means for adjusting the voltage swing of the analog output.

Latch 168 includes two octal latch circuits 168A which are preferably type 74HC564. Counters 166 include counter circuits 166A each of which is one half of an eight bit binary upcounter which are preferably type 74HC4520, NAND gates 166B which are preferably type 74HC20 and quad two input OR gates 166C which are preferably type 74HC32. The NAND gates 168B and the OR gates 168C are connected to the counter circuits 168A as shown to produce a 14 bit binary counter. DAC 170 includes the converter circuit 170A which is preferably a Burr-Brown 12 bit digital-to-analog converter type DAC80-CBI-V. Clock 174 is preferably a type 74HC4060 having a clock frequency of about 11 MHz. The divided clock frequency used to control multiplexer 158 is about 700 Hz. The parts can be purchased from one of Harris Corporation, Motorola, Inc. or Signetics Corporation among others. Operational amplifier 212 is preferably a Burr Brown type CA3140.

Power supply 200 is a conventional three terminal regulator, producing +12 V, −12 V and +5 V outputs. The positive polarity section includes a type 1N5001 diode 202, 0.1 µf capacitor to ground, a type 7812 12 V regulator 204, 0.1 µf filtering capacitor to ground and a type 7905 5 V regulator 206. The negative polarity section includes a type 1N5001 diode 202, 0.1 µf capacitor to ground, a type 7912–12 V regulator 208 and 0.1 µf filtering capacitor to ground.

Figure 7A:
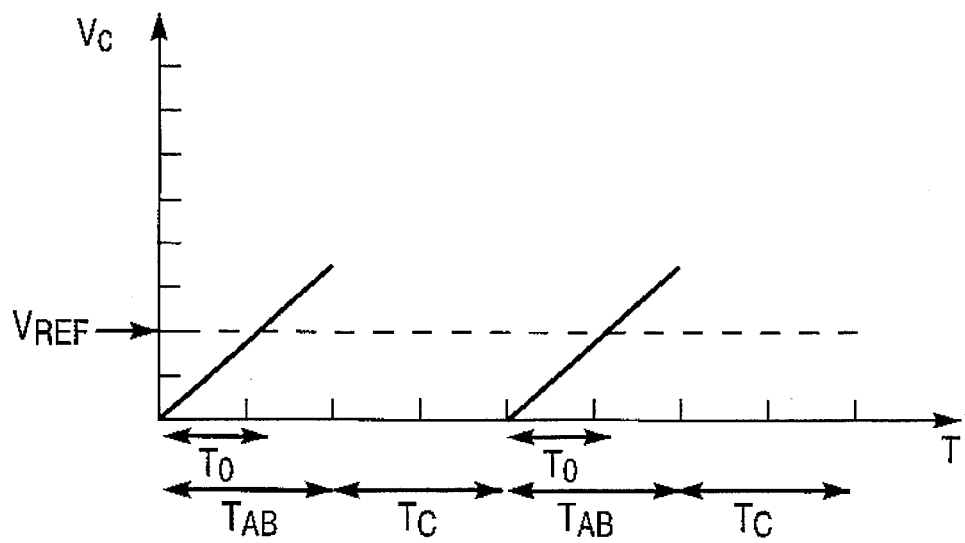
FIG. 7 is a timing diagram for the operation of the electrical circuit of FIG. 5.
Figure 7B:
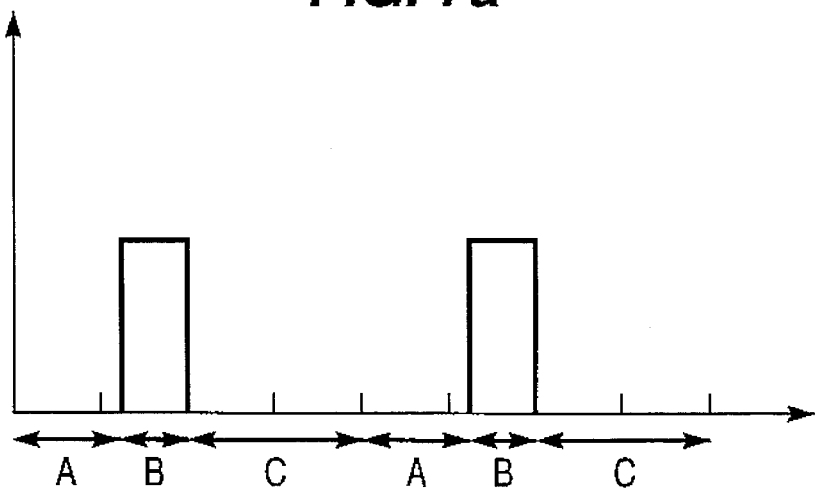

A timing diagram for the operation of the circuits of FIGS. 5 and 6 is shown in FIG. 7. In FIG. 7(a), the voltage Vc increases linearly with time T during the time interval TAB during which the multiplexer 158 connects the constant current source 152 to the capacitor 156. The time interval Tc is the alternating time interval where the multiplexer 158 connects the constant current source 152 to the reference potential. TAB is approximately equal to Tc and their sum is equal to the period of the low-frequency output of the clock 174. The time for the capacitor to charge to voltage Vref is TO<TAB. At time $T_0$, comparator 162 changes state, emitting a reset pulse which stops the counter 166 counting and causes it to reset. This is shown schematically in FIG. 7(b), where, during time interval A, counter 166 is counting. During time interval B, counter 166 is not counting. After the first cycle with the circuit of FIG. 6, the counter begins counting at the start of interval C and continues to count until the comparator changes state at the end of the next interval A. Alternatively, if the low-frequency clock pulse is OR'd (for example, using one- quarter of a 74HC32A quad 2-input OR gate) with the comparator output, and this OR'd output is used as the counter reset and latch enable, then the counter will only be counting during the voltage ramp of Vc.

Alternatively, the clock pulse can be used to prevent the counter from counting during the interval C when the capacitor is being discharged.

Figure 8:
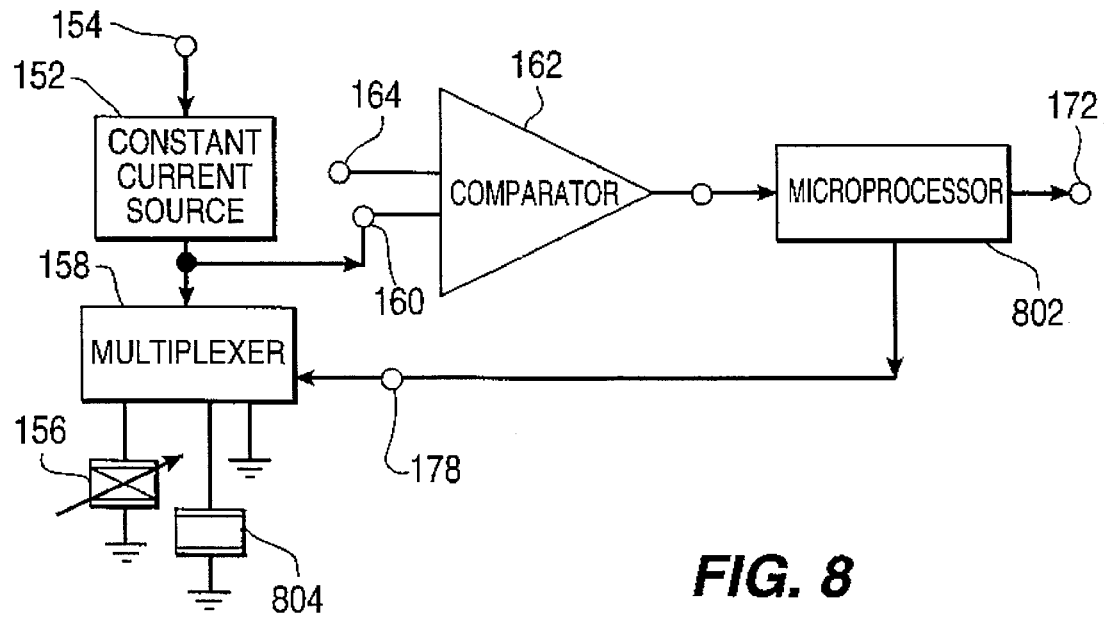
FIGS. 8 is a block diagram of another electrical circuit for measuring capacitance.

In FIG. 8 an preferred embodiment of the circuit of the invention includes a microprocessor 802 which replaces the counter, clock, and latch. By using a pulse-width-modulated output port, it can also emulate the DAC, if required. A suitable microprocessor is an Intel model 87C51FA.

In FIG. 8, the use of a reference capacitor 804 to compensate for environmental changes in the value of the capacitor 156 is shown. The multiplexer provides alternate charge/discharge cycles for both the variable capacitor 156 and the reference capacitor 804. The comparator 162 operates to generate a signal when the voltage across either capacitor exceeds $V_{ref}$. The microprocessor uses changes in the value of the reference capacitor 804 to correct the measurement of capacitor 156.

The invention is apparatus for measuring the variation in the capacitance of a capacitive sensor comprising means for charging the capacitor; means for generating an electrical signal when the capacitor is charged to a certain voltage; and means for generating an output signal corresponding to the time required to charge the capacitor to the certain voltage. In the apparatus the means for charging the capacitor comprises means for providing a source of constant electrical current to an electrode of the capacitor and the means for generating an output signal comprises comparator means for comparing the voltage on the capacitor to a reference voltage. The comparator means generates an output signal when the voltage on the capacitor is greater than the reference voltage. The means for generating an output signal may comprise means for generating a first series of timing pulses; and means for counting the first series of pulses emitted by the generating means in a given time interval. The multiplexing means alternately connects an electrode of the capacitor to the means for charging the capacitor and to a reference potential. The means for generating an output signal corresponding to the time required to charge the capacitor can be implemented using a microprocessor.

The invention is also a position sensing device having variable extension comprising capacitor means variable with extension of the device; constant current means for charging the capacitor; and means for forming an electrical output signal representative of the extension of the device. Also a method of measuring the capacitance of a capacitor comprising the steps of charging the capacitor from a constant current source; comparing the voltage developed across the capacitor to a reference voltage; generating a signal pulse once the voltage across the capacitor has reached a certain level; measuring the time required to charge the capacitor, using for example counting means; and generating an output signal linearly proportional to the charging time.

It is to be understood that the apparatus and method of operation taught herein are illustrative of the invention. Modifications may readily be devised by those skilled in the art without departing from the spirit or scope of the invention. The invention can be used as part of a position sensor or shock absorber to adjust the distance between a road surface and the chassis of a motor vehicle. The output of the sensor of the invention may be connected to a computer for controlling the leveling of a vehicle.

We claim:

1. Apparatus for measuring the capacitance of a capacitor comprising:
   means for providing a continuous source of constant electrical current to an electrode of the capacitor;
   separate means for generating a first series of timing pulses;
   comparator means for comparing the voltage on the capacitor to a reference voltage;
   means for generating an electrical signal when the comparator means indicates that the voltage on the capacitor reaches a first voltage which just exceeds the reference voltage;

means for counting the first series of timing pulses emitted by its generating means from the time that the charging of the capacitor beings until the electrical signal is generated;

means for generating an output signal corresponding to the number of timing pulses counted during the time required to charge the capacitor to the first voltage;

means for converting the total count of the first timing pulses to an output signal representative of the magnitude of the capacitor; and the comparator being connected to the counting means so that the output pulse from the comparator resets the counting means.

2. The apparatus of claim 1 further comprising multiplexing means for alternately connecting an electrode of the capacitor to the means for providing the constant electrical current to the capacitor and to the reference voltage.

3. The apparatus of claim 2 wherein the multiplexing means alternately connects the electrode of the capacitor to the means for providing the constant electrical current to the capacitor or to the reference voltage in response to a second series of timing pulses.

4. The apparatus of claim 3 wherein the second series is a submultiple of the first series.

* * * * *